(12) United States Patent
Nan et al.

(10) Patent No.: US 9,639,774 B2
(45) Date of Patent: May 2, 2017

(54) METHOD FOR DETERMINING APPLICABILTY OF A PROCESSING DEVICE, A PROCESSING PATH AND A PROCESSING PATTERN

(71) Applicant: Taiwan Semiconductor Manufacturing Company, Ltd., Hsinchu (TW)

(72) Inventors: Ching-Hsi Nan, Hsinchu (TW); Hann-Ru Chen, Hsinchu (TW); Yu-Hsiu Fu, Hsinchu (TW); Wen-Pin Liu, Hsinchu (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 767 days.

(21) Appl. No.: 13/708,864

(22) Filed: Dec. 7, 2012

(65) Prior Publication Data
US 2014/0161361 A1    Jun. 12, 2014

(51) Int. Cl.
 G06K 9/62     (2006.01)
 G01N 21/956   (2006.01)
 G06T 7/00     (2017.01)

(52) U.S. Cl.
 CPC ..... G06K 9/6202 (2013.01); G01N 21/95607 (2013.01); G06T 7/001 (2013.01); G06K 2209/19 (2013.01); G06T 2207/30148 (2013.01)

(58) Field of Classification Search
 CPC .. G06K 9/6202; G06K 2209/19; G06K 9/627; G06K 9/64; G06T 7/001; G06T 2207/30148; G01N 21/95607
 See application file for complete search history.

(56) References Cited

U.S. PATENT DOCUMENTS

| | | | | |
|---|---|---|---|---|
| 5,982,931 | A * | 11/1999 | Ishimaru | 382/218 |
| 5,985,497 | A * | 11/1999 | Phan | G03F 7/7065 382/149 |
| 6,215,127 | B1 * | 4/2001 | Yu | G03F 7/70625 250/398 |
| 6,242,270 | B1 * | 6/2001 | Nagaswami | H01L 21/67288 257/E21.525 |

(Continued)

OTHER PUBLICATIONS

ASML, "https://www.asml.com/asml/show.do?lang=EN&ctx=46437&dfp_product_id=1964".*

(Continued)

*Primary Examiner* — Dale E Page
*Assistant Examiner* — Vincent Wall
(74) *Attorney, Agent, or Firm* — McDermott Will & Emery LLP (57) ABSTRACT

The present disclosure provides a method for determining an applicability of a specific processing device having a specific processing pattern. The method includes the following steps: locating a similarity index between the specific processing pattern and a reference processing pattern of a reference processing device; and confirming the applicability of the specific processing device if the similarity index is no less than a threshold. Besides, a method for assessing an applicability of a new processing pattern for a specific processing device, and a method for determining an applicability of an alternative processing path for a reference processing path are also provided.

11 Claims, 5 Drawing Sheets (56) References Cited

U.S. PATENT DOCUMENTS

| | | | |
|---|---|---|---|
| 6,674,516 B2* | 1/2004 | Machia | G03B 27/74 355/68 |
| 6,871,114 B1* | 3/2005 | Green | G05B 19/404 700/108 |
| 7,116,816 B2* | 10/2006 | Tanaka et al. | 382/149 |
| 2001/0055415 A1* | 12/2001 | Nozaki | 382/141 |
| 2005/0281451 A1* | 12/2005 | Starikov | G05B 23/0229 382/141 |
| 2006/0186406 A1* | 8/2006 | Bushman | G01N 21/4738 257/48 |
| 2008/0316442 A1* | 12/2008 | Adel et al. | 355/52 |
| 2010/0332013 A1* | 12/2010 | Choi | G05B 23/0254 700/110 |
| 2012/0128228 A1* | 5/2012 | Fujimura et al. | 382/144 |

OTHER PUBLICATIONS

Kuijten et al., "Advanced Mix & Match Using a High NA i-line Scanner", SPIE, 25$^{th}$ Annual Inter. Symp. of Micolithography, Mar. 2000, https://staticwww.asml.com/doclib/productandservices/94105.pdf, pp. 1-12.*

Johnston, J. W., "Similarity Indices I: what do the measure?", BNWL-2152 NRC-1 addendum, Nov. 1976, pp. 1-136.*

* cited by examiner

METHOD FOR DETERMINING APPLICABILTY OF A PROCESSING DEVICE, A PROCESSING PATH AND A PROCESSING PATTERN

FIELD

The present disclosure relates to a method of accessing a processing device, a processing path and a processing pattern, and more particularly to a method of determining applicability of a processing device, a process path and a processing pattern for semiconductor manufacturing.

BACKGROUND

For semiconductor manufacturing, such as the wafer fabrication process, countless efforts are paid to achieve strict process control in all aspects including the product, process, production device, etc. The process flow for one particular product is composed of several processing paths, which starts from one end to the other end. There are certified processing devices located at the ends of a processing path. In most of the cases, each of the processing paths shall be verified before being released for production, i.e., each of the processing devices has to be certified with testing data collected from specimens processed along the processing path. If there is only one specific machine certified for one particular production at one end of a particular path, the availability of the specific machine will be critical to the productivity of the particular production. In case the specific machine is busy or repaired, the particular production will be put on hold if there is no alternative processing path.

Many of the processing devices at different ends of a processing path are different types of machines but somehow correlated in terms of a processing character. For example, a typical processing path in wafer fabrication process flow is from lithography to etching, wherein steppers and etcher are utilized at the processing steps of lithography and etching respectively, and the etching effect to a critical dimension at a particular field of the wafer can be compensated by pre-adjusting dose energy at the particular field of the wafer. According to suggestions from vendors of the processing devices, the uniformity issue due to etcher bias pattern can be improved by corrections at the dose energy map, which is employed at the lithograph process when a stepper is managed to choose dose energies to be applied at different areas (fields) of a wafer. Since the bias pattern of the each etcher is unique, the energy dose map utilized at the stepper should be based on the etcher to be selected for the subsequent etching process. Once a particular layer of a wafer is processed with a particular dose energy map, which is designed specifically for an etcher, the processing path for the wafer is then determined so that the wafer cannot be processed by any other etcher. Accordingly, there is a need to solve the abovementioned deficiencies/problems.

SUMMARY

In accordance with one aspect of the present disclosure, a method for assessing an applicability of a new processing pattern for a specific processing device is provided. The method includes steps of identifying a reference product; obtaining a specific processing pattern for the specific processing device processing the reference product, wherein the new processing pattern is developed with a reference processing device processing a new product; obtaining a reference processing pattern for the reference processing device processing the reference product; locating a similarity index between the specific processing pattern and the reference processing pattern; and comparing the similarity index with a threshold.

In accordance with another aspect of the present disclosure, a method for determining an applicability of an alternative processing path for a reference processing path is provided. The method includes locating a similarity index between the first processing pattern and the second processing pattern, wherein the alternative processing path having a first processing pattern and the reference processing path having a second processing pattern have a common end and two free ends, and a first processing device and a second processing device are located at the two free ends respectively; and confirming the applicability of the alternative processing path if the similarity index is no less than a threshold.

In accordance with one more aspect of the present disclosure, a method for determining an applicability of a specific processing device having a specific processing pattern is provided. The method includes locating a similarity index between the specific processing pattern and a reference processing pattern of a reference processing device; and confirming the applicability of the specific processing device if the similarity index is no less than a threshold.

The above objects and advantages of the present disclosure will be more readily apparent to those ordinarily skilled in the art after reading the details set forth in the descriptions and drawings that follow, in which:

DETAILED DESCRIPTION

The present disclosure will be described with respect to particular embodiments and with reference to certain drawings, but the disclosure is not limited thereto but is only limited by the claims. The drawings described are only schematic and are non-limiting. In the drawings, the size of some of the elements may be exaggerated and not drawn to scale for illustrative purposes. The dimensions and the relative dimensions do not necessarily correspond to actual reductions to practice.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

The invention will now be described by a detailed description of several embodiments. It is clear that other embodiments can be configured according to the knowledge of persons skilled in the art without departing from the true technical teaching of the present disclosure, the claimed invention being limited only by the terms of the appended claims.

Figure 1:
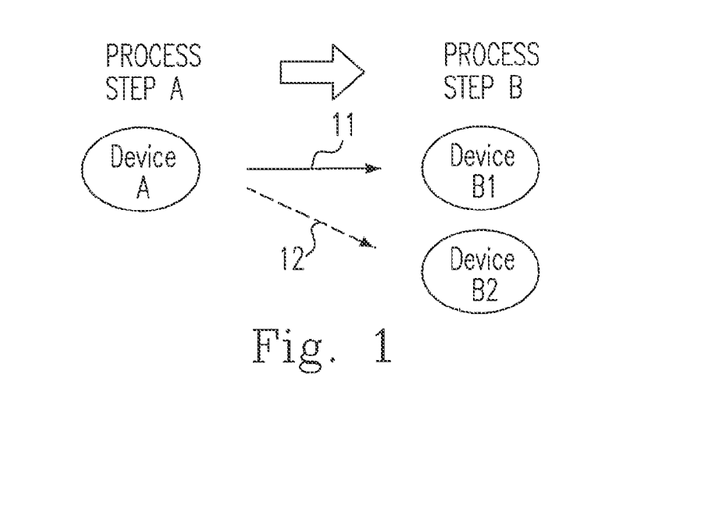
FIG. 1 is a schematic diagram showing processing paths between different process steps with different processing devices at the lower stream of the process flow.

Referring to FIG. 1, the specific processing devices A and B1 are utilized in process steps A and B respectively. A processing path 11 from the device A to the device B1 is considered a customized path applicable for a particular product. Note that the processing path 11 has been certified with the testing data collected from specimens previously processed by the device A and then by the device B1. If there exists a device B2 which is the same (or at least similar) type of the machine as the device B1, a processing path 12 indicating that the particular product is processed by the device A and then by the device B2 cannot be applicable before the processing path 12 has been certified with the testing data. In other words, for manufacturing the particular product, a production lot processed by the device A at the process step A should then be processed by the device B1 only, if the processing path 11 is the only certified processing path. It is known by the skilled person in the art that implementing a complete test production to obtain data for certifying an alternative processing path, such as the processing path 12, is extremely costly as well as time-consuming.

Figure 2:
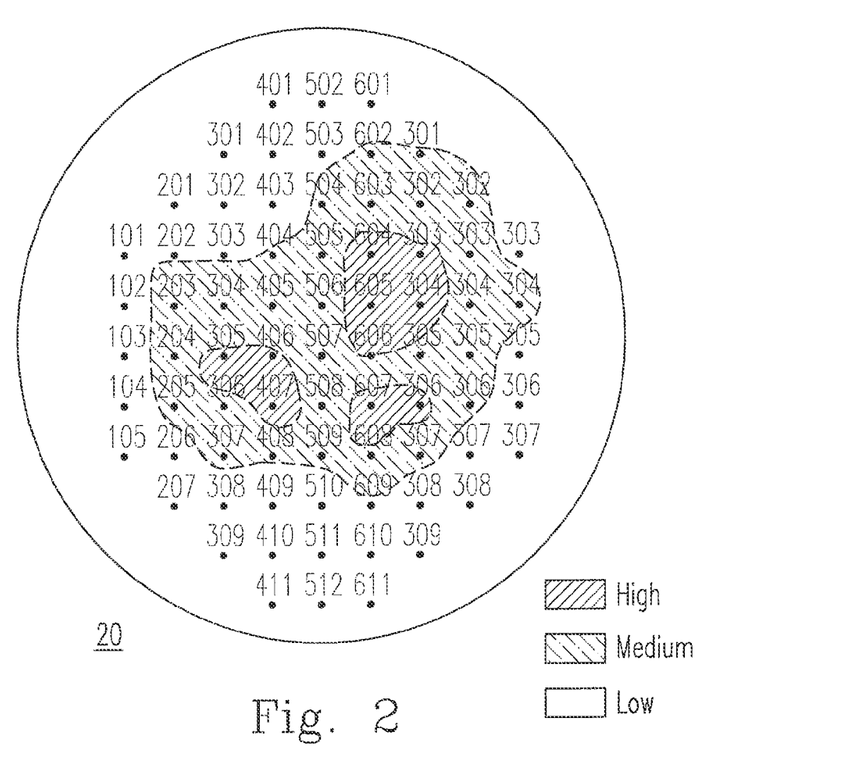
FIG. 2 is a schematic diagram showing an exemplary etching bias pattern.

Some production devices, such as etchers or CVD/PVD machines, implement a manufacturing process on a wafer layer at a period of time. The manufacturing effect, says the etching rate for instance, varies at different locations of the wafer surface. For one particular etcher, there exits a unique etcher bias pattern of the etcher when processing a particular layer of a wafer. FIG. 2 shows an example of an etcher's bias pattern 20, which is uncontrollable. It can be appreciated that the etching effect at some areas on a processed wafer layer, such as the polycrystalline silicon layer, the shallow trench isolation (STI) layer or other layers, is stronger than those at the other areas. Consequently, inspection results for critical dimensions at areas with different etching effect could be quite different, and therefore the issue of uniformity is to be resolved for the sake of better quality. It is also appreciated that referring to FIGS. 2, 3 and 5, dots with identification numbers 101, 102, etc. indicate the corresponding locations of the fields on the processed wafer layer.

Figure 7:
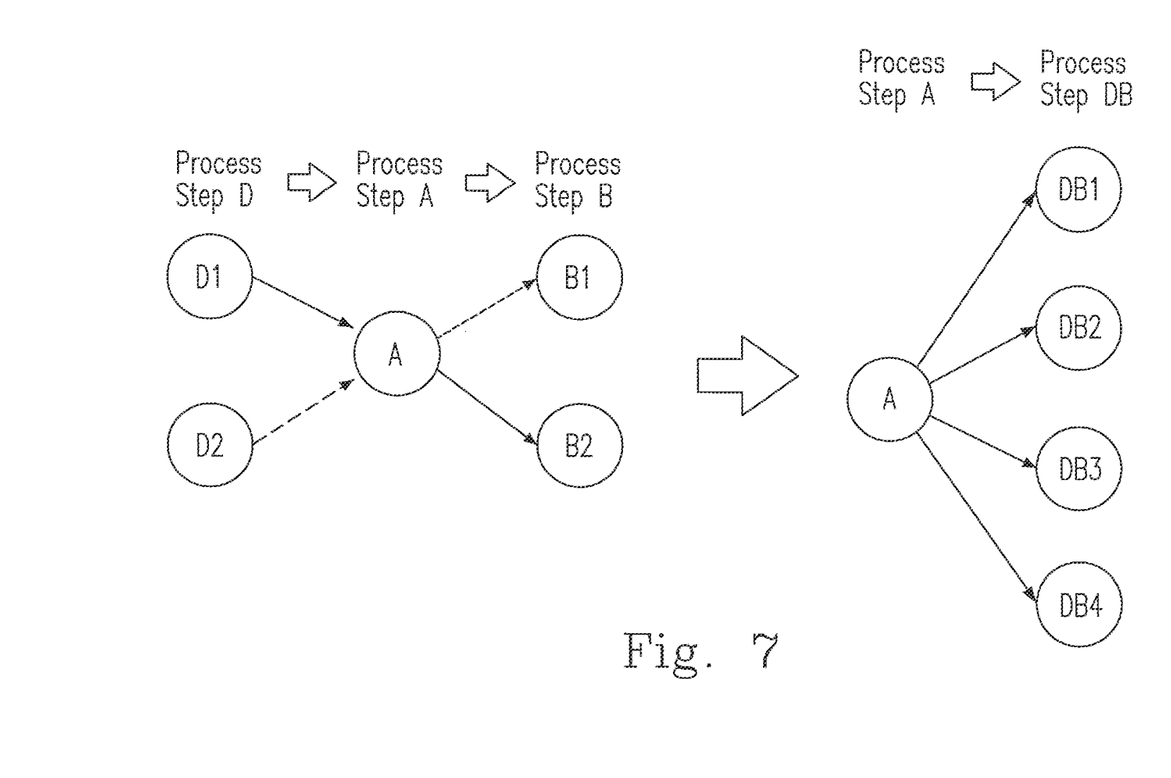
FIG. 7 is a schematic diagram showing how a process flow of three process steps can be considered as a process flow of two equivalent steps.

For the Lithography-Etch model (process A to B) or this like, the former process generate patterns for each path Ai to Bi (index of i denotes a process tool). In a more general sense, each later end of process Bi can actually represents a set of multiple process steps. One example is Diffusion—Lithography—Etch process section. Every diffusion tool, like etch tool, has its own pattern on film thickness. Film thickness pattern also affects the critical width uniformity after etch process. One can say that the after-etch critical width uniformity pattern is defined by the combination of a diffusion tool (thickness pattern) and a etch tool (etch bias pattern). The dose energy correction pattern is then designed for each set of diffusion-etch tool. We can simplify this multiple steps models, as shown in FIG. 7, to the two-layer model as in FIG. 1. The only difference therein between is that the similarity among different path is not limited to 2 process steps. The following table 1 shows the corresponding relations between the four possible process steps.

TABLE 1

| 3-Step Path and Equivalent 2-Step Path | |
|---|---|
| Three-Step Path | Equivalent Two-Step Path |
| D1 - A - B1 | A - DB1 |
| D1 - A - B2 | A - DB2 |
| D2 - A - B1 | A - DB3 |
| D2 - A - B2 | A - DB4 |

Figure 3:
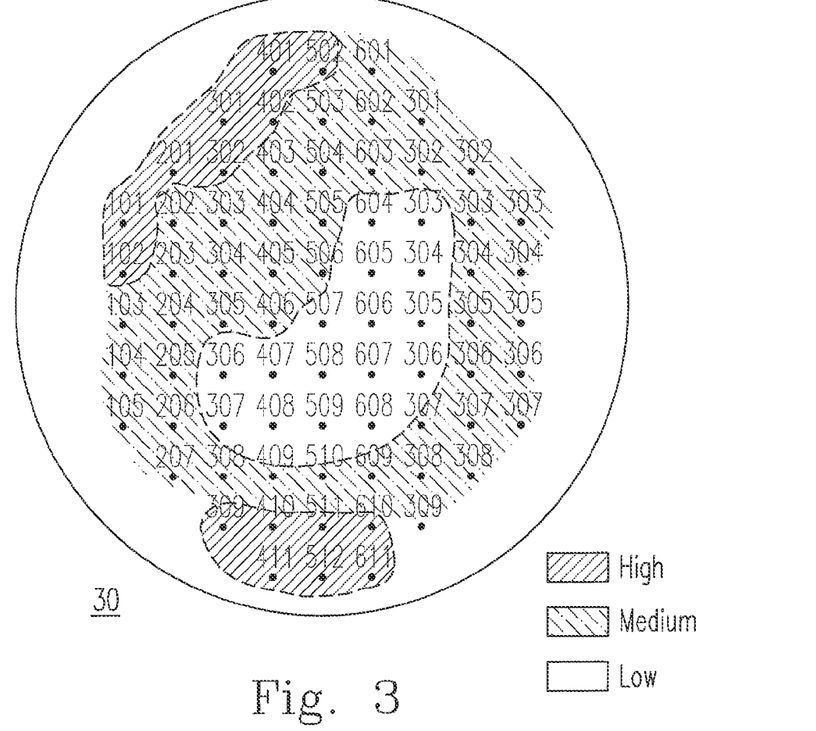
FIG. 3 is a schematic diagram showing an exemplary dose energy map.

According to the prior art set forth above, the uniformity issue due to etcher bias pattern may be improved by corrections at the dose energy map for processing the same layer of the wafer. Please refer to FIG. 3, which shows a dose energy map employed at a stepper for processing the lithography process on a wafer layer, which is usually a process step prior to etching in a processing path. Notably, the dose energy map 30 illustrated in FIG. 3 is developed based on the etcher's bias pattern 20 shown in FIG. 2, so the two patterns in a processing path are highly correlated. According to FIGS. 2 and 3, for a specific field location 101, the etching bias is at a relatively lower level while the corresponding dose energy set in the map is at a higher level, which may compensate the effect on the critical dimension due to etching bias around the field location 101. Likewise, the etching bias at the field location 605 in FIG. 2 is at a relatively higher level while the corresponding dose energy set in FIG. 3 is at a lower level, which may compensate the effect on the critical dimension due to etching bias around the field location 605.

The etcher's bias pattern 20 illustrated in FIG. 2 and the dose energy map in FIG. 3 are merely examples for describing how a pattern or map to be applied to one processing device at a particular process step is developed for correcting effect(s) made by another processing device at a different process step. The method of using adjustment or correction patterns/maps can be adopted at processing paths other than the examples set forth above. It is also notable that the actual account of bias at each field in an etcher's bias pattern can be a continuous datum rather than the discrete ones. For example in FIG. 3, the high level may range from 750 to 730, and the low level may range from 710 or below. Likewise, the indications of levels of parameters in FIGS. 2 and 5 may also indicate ranges of the parameters as shown therein.

Please refer to FIG. 1 again. For the need to improve the flexibility of production arrangement, it is required to obtain an alternative processing path 12 if there exists a device B2 which is of the same type of machine as that of the device B1 with the reasonable cost in terms of time and money as well. According to one aspect of the present disclosure, the processing paths 11 and 12 can be regarded as similar ones for performing a particular manufacturing process if the processing patterns of the processing paths 11 and 12 for a reference product are proved similar. The processing path 11 can be considered as a reference process while the processing path 12 is considered as the alternative processing path. It is appreciated that the device A is located at a common end of the two processing paths 11, 12, and the two devices B1 and B2 are located at the free ends thereof.

The processing patterns of the processing paths 11 and 12 can be obtained from samples of the reference product processed by the device B1 and the device B2 respectively.

Referring to the preceding example introduced with FIGS. 2 and 3, one may consider the process steps A and B as lithography and etching respectively, so the etcher's bias pattern 20 or the dose energy map 30 can be used as the processing pattern for determining whether the devices B1 and B2 are similar. In this embodiment, the devices B1 and B2 are etchers. For example, the dose energy map developed with samples of the reference product processed by the processing path 11 is considered as a reference processing pattern. Based on the dose energy obtained with samples of the reference product processed by the processing path 12 and the reference processing pattern, a similarity index can be calculated. If the calculation result shows that the similarity index between the two processing patterns is no less than a threshold determined based on the required quality level or confidence level, the applicability of the processing path 12 for being an alternative processing path of the processing path 11 can be confirmed, without paying efforts in doing a test production with samples to be processed along the processing path 12.

Controlling the dose energy at each field of the wafer layer is one of the available methods for compensating or pre-correcting the etching bias effect. The skilled person in the art appreciates that some other processing parameters, such as processing time in the lithography process, may also be useful for the compensation or correction. Accordingly, the type of processing patterns to be used for determining the applicability of an alternative processing path according to the preceding paragraphs is not limited to dose energy maps. Actually, any other patterns with high correlation with the etching bias pattern in terms of local processing effects may serve as the same tool to be accessed.

Figure 4:
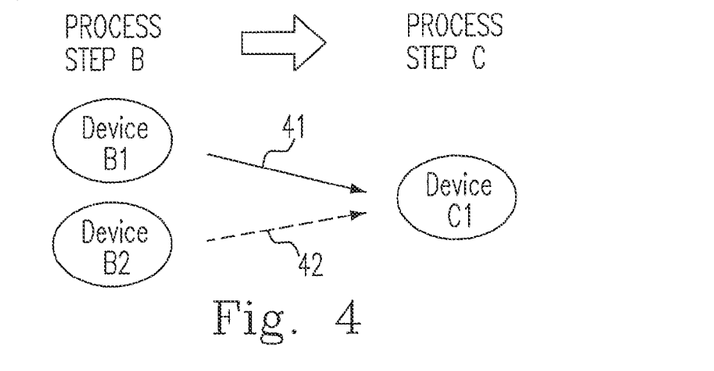
FIG. 4 is a schematic diagram showing processing paths between different process steps with different processing devices at the upper stream of the process flow.

Please refer to FIG. 4, which shows another situation when an alternative processing path or device may be considered to improve the flexibility of production arrangement. According to the illustration in FIG. 4, a processing path 41 from the device B1 in the process step B to the device C1 in the process step C is considered a customized path applicable for a particular product. For the need to improve the flexibility of production arrangement, the processing path 42 may be considered as an alternative for the processing path only if the applicability of the processing path 42 is verified with sufficient evidences such as test production data. The same concepts according to the aspect of the present disclosure introduced in the preceding paragraphs can also be applied for confirming the applicability of the processing path 42 as an alternative for the processing path 41. The processing path 41 can be considered as a reference process while the processing path 42 is considered as the alternative processing path. It is appreciated that the device C1 is located at a common end of the two processing paths 41, 42, and the two devices B1 and B2 are located at the free ends thereof.

Figure 5:
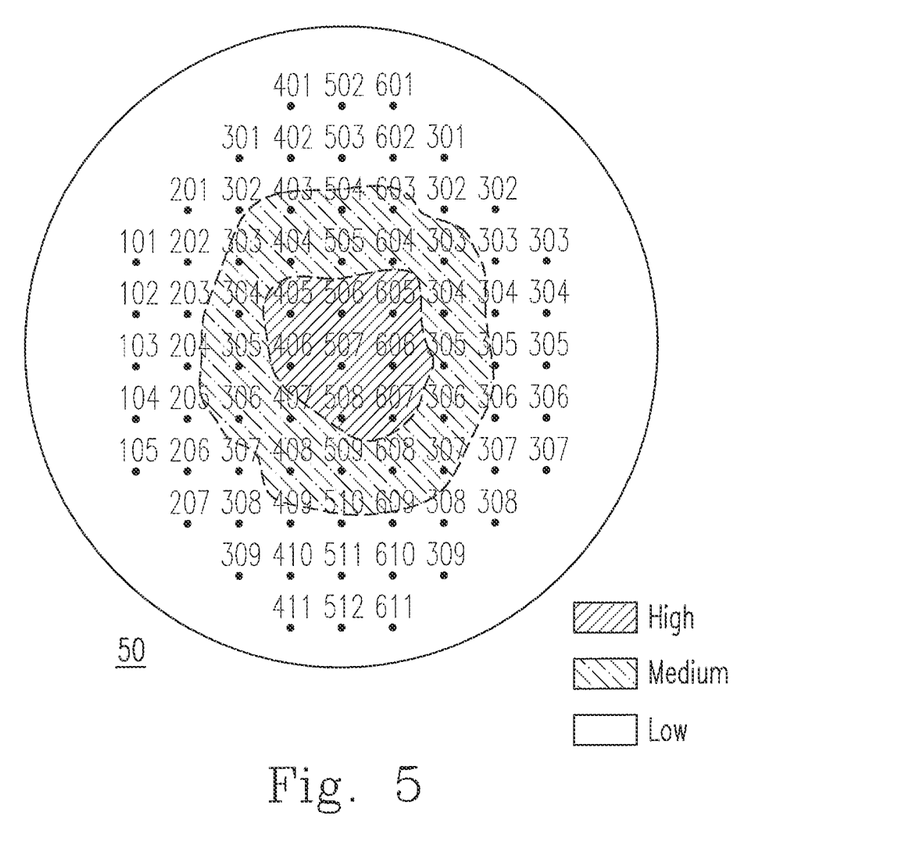
FIG. 5 is a schematic diagram showing an exemplary thin-film deposition pattern.

The processing path from etching to thin-film deposition with CVD/PVD device provides an example for the processing path 41 in FIG. 4. In this case, etching is again considered as the process step B while thin-film deposition is considered as the process step C. When taking the parameter of poly-film thickness into account, the effect due to etching bias at a particular location of the wafer layer may be either compensated or worsened by the subsequent thin-film deposition process. FIG. 5 shows an example of a deposition pattern 50 of a CVD device. The exemplary deposition pattern 50 shows that the poly-film thickness near the central area of the wafer layer is higher than those of the other areas, while there might be all different profiles as well as thickness distributions in some real cases. For the need of good uniformity of the poly-film layer, the deposition pattern 50 of the processing device C1 should match with the etching bias pattern of the etcher selected for the same processing path, either the bias pattern of the device B1 or that of the device B2. If the processing path 41 has been certified for manufacturing a particular product, one may take advantage of the concepts of the present disclosure for determining applicability of processing the device B2 or the processing path 42 based on the similarity between the etching bias patterns of the devices B1 and B2, or the thin-film deposition patterns developed for the processing paths 41 and 42, since the etching bias pattern and the thin-film deposition pattern for the same processing path shall be highly correlated. According to the above, the selection of the alternative processing path is based on the similarity index between the processing patterns of two process devices utilized in the process step at either the upper stream or the down stream of the process flow.

According to one embodiment of the present disclosure, the method of locating the value of the similarity index between two processing patterns can be based on correlations of the relative locations of the two processing patterns. Please refer to FIGS. 2, 3 and 5 again in which dots with identification numbers 101, 102, etc. also indicate the corresponding locations of each of the processing patterns. Assuming that $a_i$ and $b_i$ denote values of processing parameters, such as the etching bias, processing time, dose energy, deposition thickness, etc., at the corresponding location i in the processing patterns A and B respectively, the similarity index therebetween may be determined by calculating a correlation per the following formula, where the symbols $\mu$ and $\sigma$ denote the average and the standard deviation respectively:

$$\text{Similarity index} = \Sigma(a_i-\mu_a)*(b_i-\mu_b)/(n-1)*\sigma_a*\sigma_b \qquad (1)$$

It is appreciated by the skilled person in the art that the value of the similarity index calculated based upon formula (1) should fall in a range of −1 to 1. When a value of the similarity index is higher than 0.9, the two patterns can be considered highly correlated. On the other hand, when a value of the similarity index is lower than 0.65, the correlation relationship between the two patterns should be not significant. Therefore, a threshold ranging from 0.65 to 0.9 can be chosen for judging the similarity between the two patterns, depending on the required quality level or confidence level. Besides, the similarity index may be obtained from methods other than the correlation method described above, as long as a threshold value therefor can be specified.

According to another aspect of the present disclosure, the method set forth above may be used for assessing the applicability of a processing device or a processing pattern. For example, referring to FIG. 4, the present disclosure is also good for determining the applicability of the device B2 as an alternative processing device for the device B1 when the alternative processing path 42 is accessed. Likewise, if two processing patterns for manufacturing a reference product at two devices, says B1 and B2, are considered as similar based on a reasonably high similarity index, a new processing pattern for the device B1 to process a specific product can be considered applicable for the device B2 to process the specific product.

Figure 6:
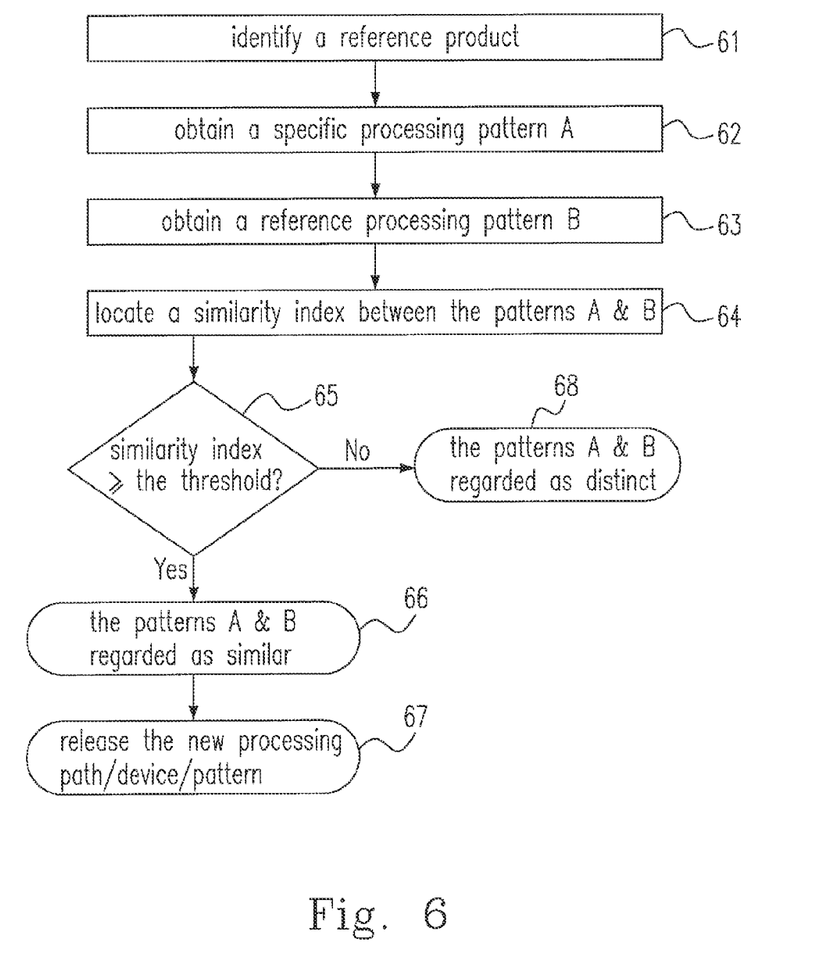
FIG. 6 is a flowchart showing a method for determining applicability of a processing path, a processing device or a processing pattern, according to some embodiments of the present disclosure.

Please refer to FIG. 6, which is a flowchart showing a method for determining applicability of a processing path, a processing device or a processing pattern, according to one embodiment of the present disclosure. The main idea for adopting the method is to make use of existing data related to a reference product in the production line, so firstly the reference product has to be identified (Step 61). According to the descriptions set forth above, the processing device and the processing pattern can be a doper and a dose energy map respectively, or, the processing device and the processing pattern can be a CVD/PVD machine and a deposition pattern respectively. Besides, the processing path may consist of two or more processing steps.

For the purpose of determining the applicability of an alternative processing path/device/pattern, a specific processing pattern A used for processing the reference product at the alternative processing path/device is obtained (Step 62), and then a reference processing pattern B used for processing the reference product at the reference processing path/device is obtained (Step 63). Practically, the specific processing pattern A and the reference processing pattern B are of the same type of processing patterns. It would be cost-effective if the processing patterns are retrievable from the existing data base. Step 63 is not necessarily a consequent step of Step 62. Notably, the choice of the reference product at Step 61 may not be necessary for determining the applicability of an alternative processing path or an alternative processing device if the processing patterns A and B are not product-specific patterns, i.e., the processing patterns A and B are common processing patterns for different products.

After data related to the two patterns A and B are obtained, one may locate a similarity index based on the two patterns A and B (Step 64). The similarity index can be determined by calculating a correlation between the specific processing pattern and the reference processing pattern. The calculation can be based on the formula (1) as described in the preceding description, or other applicable method known to the art. Further, the correlation between the specific processing pattern and the reference processing pattern is calculated based upon a processing index at corresponding locations. The processing index may be, but not limited to, dose energy, deposition thickness, processing time, or a combination thereof. Preferably, the processing index selected for the calculation of the correlation or similarity index is related to the control for critical dimension(s), so the quality of the semiconductor products can be managed properly.

When the value of the similarity index is located, the next step is to compare the value of the similarity index with a pre-determined threshold (Step 65). Based on the required confidence level, the threshold may be selected within a range from 0.65 to 0.9. If the similarity index is no less than the threshold, the two patterns A and B are regarded as similar (Step 66), and therefore the new processing path/device/pattern is confirmed applicable and to be released for production (Step 67). Otherwise, the two patterns A and B are regarded as distinct so that the processing path/device/pattern being assessed cannot be an alternative in this regard (Step 68).

If a new processing path is considered as an alternative one for a specific processing path, it will be more flexible for process control management with dealing with the arrangement for the specific processing path. On the other hand, if two processing paths are considered as alternative for each other, the total number of controlled processing paths or customized processing paths may be reduced by one. One may reduce the total number of controlled processing paths or customized processing paths by continually repeating the abovementioned method. Consequently, the total number of controlled processing paths or customized processing paths will be reduced, and so is the cost as well as efforts to by paid for the production control.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims that are to be accorded with the broadest interpretation so as to encompass all such modifications and similar structures.

What is claimed is:

1. A method, comprising:
   processing a first semiconductor product along a reference processing path to form a first processing pattern on the first product;
   processing a second semiconductor product along an alternative processing path to form a second processing pattern on the second product;
   determining a similarity index quantifying a similarity between the first processing pattern and the second processing pattern,
   wherein the similarity index=$\Sigma(a_i-\mu_a)*(b_i-\mu_b)/(n-1)*\sigma_a*\sigma_b$,
   wherein $a_i$ and $b_i$ are values of processing parameters at a corresponding location i in the specific processing pattern and reference processing pattern, respectively,
   $\mu_a$ and $\mu_b$ are the average value of the processing parameters of the specific processing pattern and the reference processing pattern, respectively, and
   $\sigma_a$ and $\sigma_b$ are the standard deviation of the processing parameters of the specific processing pattern and the reference processing pattern, respectively,
   wherein the alternative processing path and the reference processing path have a common end and first and second respective free ends,
   wherein the first free end comprises a first tool and the second free end comprises a second tool,
   wherein the common end comprises a third tool,
   wherein the first tool and the second tool are either an etcher or a deposition tool, and
   wherein the third tool is a stepper or an etcher; and
   confirming applicability of the alternative processing path if the similarity index is no less than a threshold, wherein the threshold ranges between 0.65 and 1.

2. The method as claimed in claim 1, wherein the processing parameter includes one selected from a group consisting of a dose energy, a deposition thickness, a processing time and a combination thereof.

3. The method as claimed in claim 1, wherein the processing parameter is related to a control for a width uniformity at corresponding locations on processed wafer layers of the first and second semiconductor products.

4. The method as claimed in claim 1, wherein the first processing pattern includes one of a dose energy map and a deposition pattern.

5. A method, comprising:
   generating a specific processing pattern on a first product by processing a first semiconductor wafer using a specific processing device and an additional processing device;
   generating a reference processing pattern on a second product by processing a second semiconductor wafer with a separate reference processing device and the additional processing device;
   determining a similarity index that quantifies a similarity between the specific processing pattern and a reference processing pattern, wherein the similarity index=$\Sigma(a_i-\mu_a)*(b_i-\mu_b)/(n-1)*\sigma_a*\sigma_b$, wherein $a_i$ and $b_i$ are values of processing parameters at a corresponding location i in the specific processing pattern and reference processing pattern, respectively, $\mu_a$ and $\mu_b$ are the average value of the processing parameters of the specific processing pattern and the reference processing pattern, respectively, and $\sigma_a$ and $\sigma_b$ are the standard deviation of the processing parameters of the specific processing pattern and the reference processing pattern, respectively, the processing index includes one selected from a group consisting of a dose energy, a deposition thickness, a processing time and a combination thereof; and confirming applicability of the specific processing device if the similarity index is no less than a threshold, wherein the threshold ranges between 0.65 and 1.0.

6. The method as claimed in claim 5, wherein the processing index is related to a control for a width uniformity at corresponding locations on the first and second semiconductor wafers.

7. The method as claimed in claim 5, wherein the specific processing device comprises a first etcher, wherein the reference processing device comprises a second etcher, and wherein the additional processing device comprises a stepper.

8. The method as claimed in claim 5, wherein the specific processing pattern includes one of a dose energy map and a deposition pattern.

9. A method, comprising:
performing a first process of either lithography or etching on a first semiconductor wafer using a first tool, wherein the first tool is a stepper or an etcher;
performing the first process on a second semiconductor wafer using the first tool;
performing a second process of either etching or deposition on the first semiconductor wafer using a second tool to form a first semiconductor product, the first semiconductor product having a specific processing pattern generated by the first tool and the second tool, wherein the second tool is an etcher or a deposition tool;
performing the second process on the second semiconductor wafer using a reference tool to form a reference processing pattern of a second semiconductor product, the reference processing pattern generated by the first tool and the reference tool, wherein the reference tool is separate from the second tool,
wherein the reference tool is an etcher when the second tool is an etcher or a deposition tool when the second tool is a deposition tool;
determining a similarity index that quantifies a similarity between the specific processing pattern and the reference processing pattern,
wherein the similarity index=$\Sigma(a_i-\mu_a)*(b_1-\mu_b)/(n-1)*\sigma_a*\sigma_b$,
wherein $a_i$ and $b_i$ are values of processing parameters at a corresponding location i in the specific processing pattern and reference processing pattern, respectively,
$\mu_a$ and $\mu_b$ are the average value of the processing parameters of the specific processing pattern and the reference processing pattern, respectively, and
$\sigma_a$ and $\sigma_b$ are the standard deviation of the processing parameters of the specific processing pattern and the reference processing pattern, respectively,
comparing the similarity index with a threshold, wherein the threshold ranges between 0.65 and 1; and
confirming applicability of the second tool if the similarity index is greater than or equal to the threshold.

10. The method as claimed in claim 9, wherein the processing parameter includes one selected from a group consisting of a dose energy, a deposition thickness, a processing time and a combination thereof.

11. The method as claimed in claim 9, wherein the specific processing pattern and the reference processing patterns are dose energy maps.

* * * * *